United States Patent

Alberti et al.

[11] Patent Number: 5,166,380
[45] Date of Patent: Nov. 24, 1992

[54] MESOPOROUS CRYSTALLINE SOLID COMPOUND OF A DIPHOSPHONATE/PHOSPHITE OF A TETRAVALENT METAL, WITH A NARROW DISTRIBUTION OF MESOPORES

[75] Inventors: Giulio Alberti; Umberto Costantino; Riccardo Vivani, all of Perugia; Piergiorgio Zappelli; Antonio Rossodivita, both of Monterotondo; Luciano Bassignani, Passo Corese, all of Italy

[73] Assignee: Eniricerche S.p.A., Milan, Italy

[21] Appl. No.: 738,891

[22] Filed: Aug. 1, 1991

[30] Foreign Application Priority Data

Aug. 3, 1990 [IT] Italy .................. 21213 A/90

[51] Int. Cl.$^5$ .................................. C07F 7/00
[52] U.S. Cl. ........................... 556/19; 556/13; 556/51; 556/54
[58] Field of Search ............... 556/54, 51, 13, 19, 556/81

[56] References Cited

U.S. PATENT DOCUMENTS 4,374,242 2/1983 Dines et al. .................. 556/13 X

*Primary Examiner*—Arthur C. Prescott
*Attorney, Agent, or Firm*—Shea & Gould

[57] ABSTRACT

The present invention discloses a compound comprising a diphosphonate/phosphite of a tetravalent metal:

$$M[(O_3P-R-PO_3)_{1-(x+y)}(HPO_3)_{2x}(O_3P-R-PO_3H_2)_{2y}]$$

(where M, R, x and y have the meaning given in the description), in the form of a crystalline solid with an alpha-type lamellar structure with a distance between layers of 7.4 to 20Å (depending on the dimensions of radical R), a BET surface area of 250 to 400m$^2$/g, and porosity within the mesopore range, with at least 50% of the pores measuring 20 to 30Å. The compound, depending on the radical R used, may or may not have microporosity in the region between layers. Such a diphosphonate/phosphite of a tetravalent metal is obtained by reaction between diphosphonic acid, phosphorous acid and an oxyhalide of a tetravalent metal, in a solvent comprising dimethyl-sulphoxide/water containing hydrofluoric acid.

13 Claims, 5 Drawing Sheets

MESOPOROUS CRYSTALLINE SOLID COMPOUND OF A DIPHOSPHONATE/PHOSPHITE OF A TETRAVALENT METAL, WITH A NARROW DISTRIBUTION OF MESOPORES

The present invention relates to a mesoporous crystalline solid compound comprising a diphosphonate/phosphite of a tetravalent metal, with a narrow distribution of mesopores, the process for its production and its uses.

Figure 1:
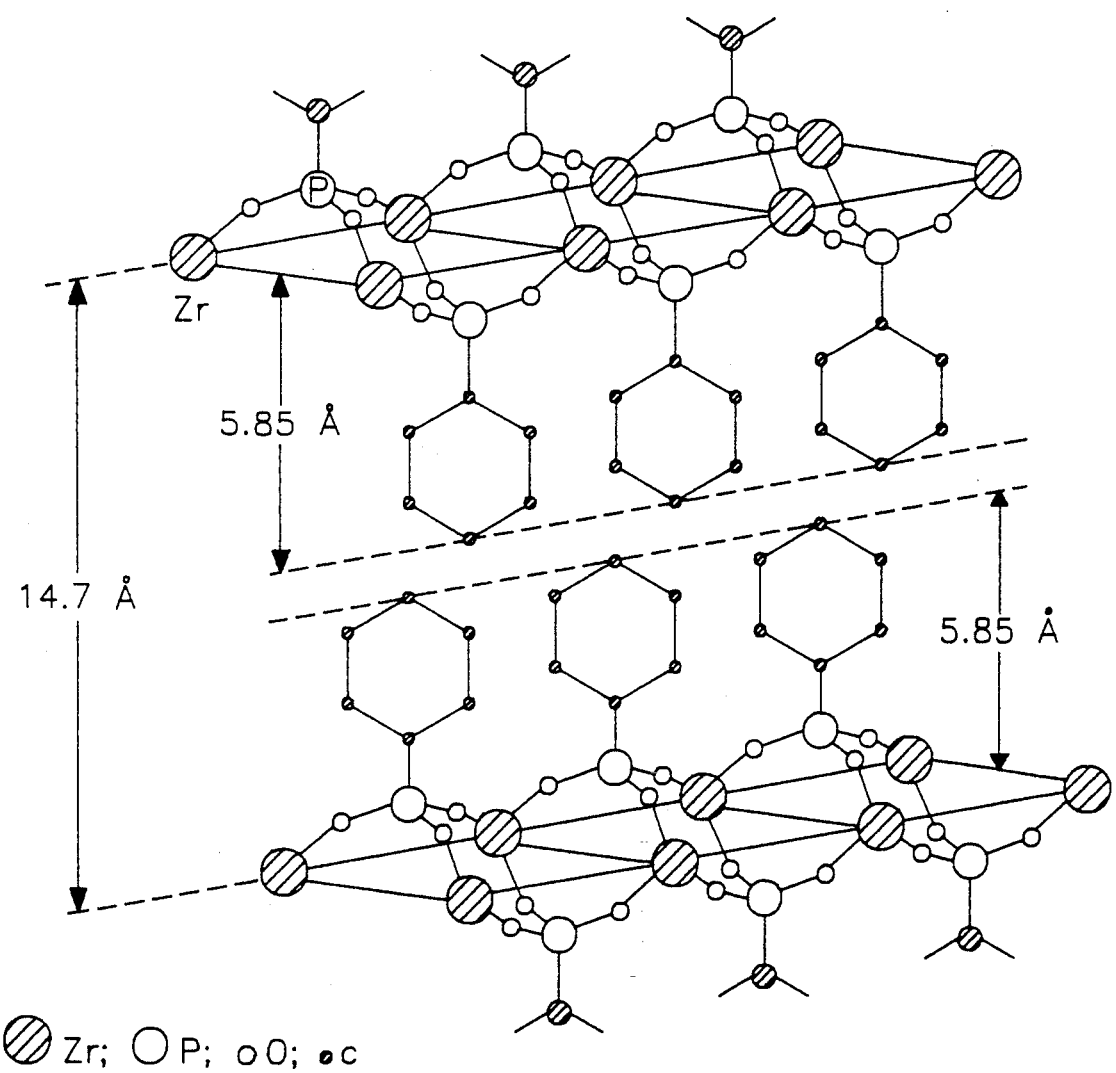

G. Alberti, S. Allulli, U. Costantino and N. Tomasini, in J. Inorg. Nucl. Chem., 40, 1113 (1978), described the process for obtaining lamellar compounds, with a structure similar to that of zirconium alpha-phosphate [alpha-Zr(HPO$_4$)$_2$.H$_2$O], by reaction between phosphonic acids and salts of tetravalent metals. These lamellar phosphonates can be represented with the general formula M(RPO$_3$)$_2$, where M is a tetravalent metal and R is an organic radical. A specific example is zirconium benzene-phosphonate, the structure of which is shown in FIG. 1.

After this basic discovery, intense research was conducted within this field due to the considerable potential applications of the compounds obtained and in particular we would quote the following technical and patent literature: G. Alberti, U. Costantino and M. L. Luciani, J. Chromatog., 180, 45 (1979); G. Alberti and U. Costantino, J. Mol. Catal., 27, 235 (1984); G. Alberti, U. Costantino, J. Korney and M. L. Luciani, Reactive Polymers, 4, 1 (1985); G. Alberti, U. Costantino and G. Perego, J. Solid State Chem., 63, 455 (1986); EP 10.366; EP 10.857; M. B. Dines and P. M. Di Giacomo, Inorg. Chem. 20, 92 (1981); P. M. Di Giacomo and M. B. Dines, Polyhedron, 1, 61 (1982); M. B. Dines, P. M. Di Giacomo, K. P. Collahan, P. C. Griffith, R. H. Lane and R. E. Cooksey, ACS Series 192, Chpt. 13, ACS, Washington, D.C., 1982; M. B. Dines, R. E. Cooksey, P. C. Griffith and R. H. Lane, Inorg. Chem. 22, 1003 (1983); M. B. Dines and P. C. Griffith, Polyhedron 2, 607 (1983), C. Y. Ortiz-Avila and A. Clearfield, Inorg. Chem. 24, 1773 (1985); A. Clearfield, Design of New Materials, Plenum Press, New York (1987), P. 121-134 and A. Clearfield, Chem. Rev. 88, 125 (1988).

Figure 2:
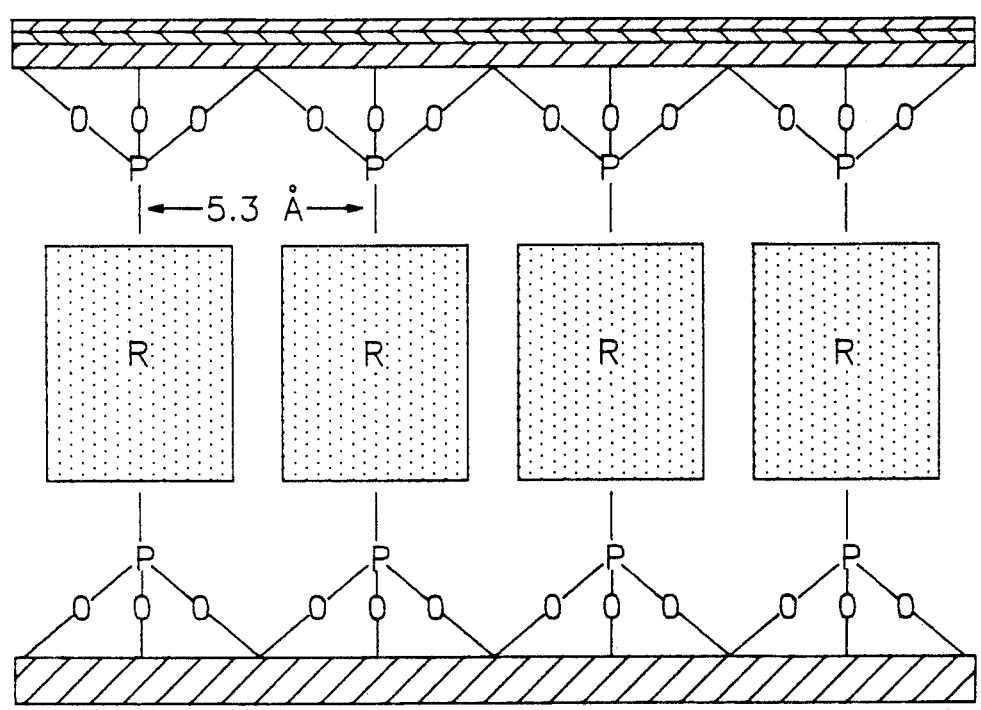
Figure 3:
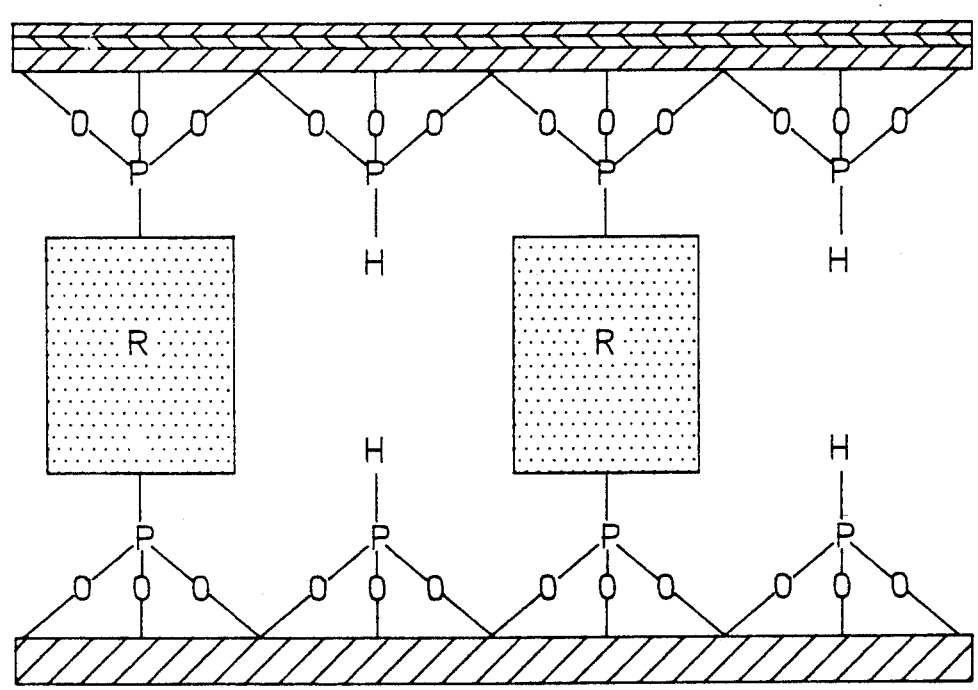

In EP 10.366 and EP 10.857 some "pillared" compounds are described, obtained by reaction between salts of tetravalent metals and diphosphonic acids, with a formula M$^{IV}$R(PO$_3$)$_2$, (where M is a tetravalent metal and R is a bivalent organic radical), the structure of which is given schematically in FIG. 2. Unfortunately, given the alpha-structure of the layers, the distance between the central axes of adjacent pillars is only 5.3 Å. Considering that the average van der Waals diameter is about 4.4 Å for pillars made up of aliphatic chains and about 3.7 Å for pillars made up of aromatic rings, it is possible to deduce that the free space between pillars is smaller than the diameter of the molecules and therefore the compounds obtained are of no use as molecular sieves. In order to introduce a certain degree of microporosity between the layers it has proposed to dilute the pillars replacing them partly with very small R'—PO$_3$ type groups, for example H—PO$_3$, HO—PO$_3$ and CH$_3$—PO$_3$ (see for example Clearfield, quoted above). The formation of a microcavity in an idealized compound, by introducing phosphite groups, is shown schematically in FIG. 3. In these compounds the dimensions of the cavity depend essentially on the length of the R(PO$_3$)$_2$ pillar and the spacing between the pillars.

However, in the state of the art the problems relating to obtaining a compound which has not only a high porosity in the region between layers, but also a narrow distribution of the diameter of the pores have not yet been overcome. In particular, the Applicants have carried out some preliminary studies on diphosphonic acid/phosphorous acid/zirconium salt systems and reached conclusions similar to those of Clearfield, quoted above, namely that the molar fraction of R(PO$_3$)$_2$ groups that can be replaced by H—PO$_3$ gradually becomes smaller as the degree of crystallinity increases, since there is a strong tendency towards the segregation of the two phases, one comprising Zr(HP—O$_3$)$_2$ only and the other comprising zirconium diphosphonate containing only a few phosphite groups. For example, it has been discovered experimentally that while in amorphous or semi-crystalline zirconium diphosphonates it is not difficult to achieve substitutions of up to 40-50% of the R(PO$_3$)$_2$ groups, this percentage falls drastically to only 5-15% in compounds with a high degree of crystallinity. Consequently, the synthesis processes described in the literature enable considerable microporosity to be achieved for spacing with HPO$_3$ groups only when the pillared compounds are prepared with a low degree of crystallinity. In such circumstances, however, as was to be expected given the irregularity of the substitutions and as found by Clearfield, quoted above, it is not possible to achieve a narrow distribution of micropores in the region between layers, this being a very important condition for the use of these compounds as molecular sieves and/or as catalysts for shape selective catalysis.

It has now been discovered that it is possible to prepare a diphosphonate/phosphite of a tetravalent metal, in crystalline form, in such conditions that the HPO$_3$ groups, in addition to forming or not forming micropores in the region between layers, also cause the formation of a quantity of mesopores. It was also noted with surprise that such mesoporosity is not of a random type, as is usually obtained in many micro-crystalline compounds, but has a very narrow distribution with most of the pores within the range of 20-30 Å. Such porosity cannot, therefore, be attributed to the formation of cavities in the region between layers as described in the state of the art literature, such as EP 10.336 and EP 10.857, since the dimensions of the pores are not related to the length of the R(PO$_3$)$_2$ pillar and the Applicants have experimentally observed in some cases pore dimensions of 4-8 times larger than the distance between layers in the zirconium diphosphonate/phosphite. On the other hand a high percentage of porosity with dimensions of 20-30 Å cannot be attributed to the spacing between pillars either if we consider for example that the average distance between the central axes of adjacent pillars of a zirconium diphosphonate with an alpha structure in which 66% of the pillars is replaced by phosphite groups is only 9.2 Å it becomes clear that the average distance cannot be more than 6 Å.

One of the aims of the present invention is therefore a new diphosphonate/phosphite mesoporous crystalline solid compound of a tetravalent metal, with a narrow distribution of mesopores.

Another aim of the present invention is the process for the preparation of such crystalline solid compound.

An additional aim of the present invention is the use of the said compound.

Other aims of the present invention shall become clear from the description that follows.

In particular, the compound covered by the present invention is a diphosphonate of a tetravalent metal containing acid phosphite groups and diphosphonate groups fixed to the surface, which can be defined with the general formula:

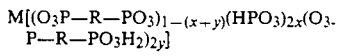

where:

M is a tetravalent metal;
R is a bivalent organic radical;
x varies from 0.3 to 0.45; and
y varies from 0.05 to 0.2;
the compound being in the form of a crystalline solid having the following characteristics:
an alpha type lamellar structure with a distance between layers of 7.4 to 20 Å;
a BET surface area of 250 to 400 m$^2$/g; and
porosity within the mesopore range, with at least 50% of the pores measuring 20 to 30 Å.

In particular, in the above formula, M is a tetravalent metal that may be appropriately selected from zirconium, titanium and tin, and preferably will be zirconium due to the greater stability to hydrolysis of the corresponding compound. The bivalent organic radical R will appropriately be a very short radical so as to form in the region between layers micropores which are so small as to be inaccessible to common molecules. Alternatively, non-rigid R radicals may be used, such as the aliphatic chains, which tend to occupy the voids created by the small dimensions of $HPO_3$ groups, with a consequent reduction in the distance between layers. In accordance with this, R shall be selected from the aliphatic bivalent organic radicals containing in the molecule from 2 to 10 carbon atoms, or aromatic with 1 to 2 uncondensed rings, or from the alkyl-aromatic radicals. Specific examples of the R radical are $-CH_2-CH_2-$, $-CH_2-(CH_2)_2-CH_2-$, $-CH_2-(CH_2)_4-CH_2-$, $-C_6H_4-$, $-C_6H_4-C_6H_4-$ and $-CH_2-C_6H_4-C_6H_4-CH_2-$. Preferred examples of R radicals are $-C_6H_4-$, $-C_6H_4-C_6H_4-$, and $-CH_2-C_6H_4-C_6H_4-CH_2-$.

In the compound covered by the present invention the specific value of the distance between layers depends on the R radical and, depending on the particular R radical selected, the compound may or may not have a microporosity in the region between layers. Furthermore, in the above formula the value 2y refers to the quantity of acid diphosphonate groups present on the surface, with the specific value of y depending on the surface area.

More particularly, the compound covered by the present invention is a crystalline solid in which x varies from 0.3 to 0.45, and the groups present on the surface may be either the phosphites or the diphosphonates. The latter differ from those inside since one of their two phosphonic groups is in an acid form and due to their presence make the total phosphorus/zirconium (or other tetravalent metal) ratio more than 2, the latter being the typical value of alpha-type lamellar compounds. The quantity of acid diphosphonate groups depends on the surface extension and may be determined by titrating the crystalline solid, dispersed in a solution of NaCl (0.1-1M) with sodium hydroxide up to pH 7. The values of y vary from 0.05 to 0.2 depending on the surface extension. Furthermore, the compound is an alpha-type lamellar solid with a distance between layers of 7.4 to 20 Å or more, depending on the dimensions of the R radical with a BET surface area of 250 to 400 m$^2$/g, with porosity within the mesopore range and with at least 50% of the pores measuring 20 to 30 Å. The compound, depending on the R radical used, may or may not have microporosity in the region between layers.

The present invention also relates to a process for the preparation of the diphosphonate-phosphite compound described above essentially comprising the reaction between a diphosphonic acid $R(PO_3H_2)_2$, phosphorous acid $H_3PO_3$ and an oxychloride of tetravalent metal $MOCl_2$, in a solvent comprising sulphoxide/water containing hydrofluoric acid:

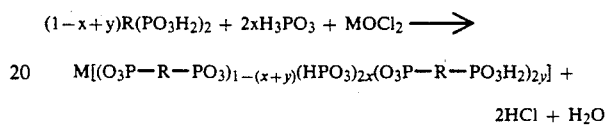

(where M, R, x, y have the meaning given above). Specific examples of diphosphonic acids $R(PO_3H_2)_2$ suited for the purpose are 1,4-benzene-diphosphonic acid, 4,4'-bis (phosphono-methyl) biphenyl acid and 4,4'-bis (biphenyl) diphosphonic acid, the synthesis and use of which shall be described in detail in the experimental examples that follow. The preferred tetravalent metal oxychloride is octahydrate $ZrOCl_2.8H_2O$ zirconyl chloride and monohydrate $ZrOCl_2.H_2O$ zirconyl chloride.

In the reaction the molar ratio between the phosphorus acids (diphosphonic acid plus phosphorous acid) and the tetravalent metal oxychloride is 2:1 to 20:1. As hydrofluoric acid a concentrated aqueous solution of the acid is used, with a molar ratio of 6:1 to 30:1 as regards the zirconium or other tetravalent metal. The reaction medium is important in the process covered by the present invention. Many of the solvents used in the known state of the art to achieve microporosity in the region between layers (water, alcohols, acetonitrile, etc.) are ill-suited to obtaining mesoporous compounds. By contrast, sulphoxide solvents, especially dimethylsulphoxide mixed with water, are particularly effective in obtaining the compound covered by the present invention. The reaction temperature may vary from 10° to 130° C. and the reaction times may vary from 10 to 100 hours. Typically the operating temperature is in the order of 80° C., for a time of about 24 hours. At the end of the reaction the diphosphonate/phosphite compound of tetravalent metal is separated, in the form of a microcrystalline solid, which is recovered by filtration or centrifugation, washed with organic solvent and dried.

The mechanism whereby the presence of phosphorous acid in the reaction environment chosen causes the formation of mesopores is not clear. In fact, if these mesopores originate from the packing of lamellar micro-crystals one would expect such formation even in the absence of phosphite groups. The experiments carried out by the Applicants have shown, however, that in the absence of phosphite relatively much smaller surface areas are obtained and with a very wide distribution of mesopores. A narrow distribution of pores was not therefore to be expected given the random nature of the packing and the different dimensions of the lamellar micro-crystals. Without commitment to any one particular theory, it is considered that the presence of phosphorous acid in the conditions of synthesis of diphosphonates encourages the formation of thin lamellas of more or less uniform dimensions and encourages their regular packing and/or creates large gaps within the crystal preventing the growth of some of its layers. In any case, whatever the mechanism of the formation of mesoporosity, this phenomenon is clearly distinct from that of the creation of microcavities which is achieved by operating in accordance with the known state of the art. In particular, in EP 10.366 and EP 10.857, quoted above,
the aim is to obtain compounds with high microporosity, of the type schematically illustrated in FIG. 3, whereas according to the present invention the aim is to obtain compounds with the lowest possible percentage of micropores in the region between layers, so as to have compounds essentially containing mesopores only. For this reason diphosphonates with a small or non-rigid R radical are used, as previously stated.

Given the narrow distribution of mesopores within the region of 20–30 Å, the solid crystalline compounds of the present invention are of considerable interest as molecular sieves for large molecules. Furthermore, by making these pores functionalized by introducing catalytically active groups, the present compounds may form the basis for the production of shape selective catalysts.

The experimental examples that follow are given further to illustrate the present invention.

EXAMPLE 1

Preparation of Mesoporous Benzene-Diphosphonate/Phosphite of Zirconium a) Preparation of 1,4-Benzene-Diphosphonic acid tetra-ethyl ester 10 g (42 mmoles) of 1,4-dibromo-benzene and 600 mg of anhydrous $NiCl_2$ are placed in a two-necked 250 ml flask which has a cooler, dripper funnel and magnetic agitation. 17.6 ml (100 mmoles) of triethyl-phosphite are added to the mixture dropwise and heated to 170° C. in an oil bath. The mixture is left under agitation at 170° C. for 2 hours, it is then cooled to 100° C. and subjected to vacuum distillation (1 mm Hg) to eliminate the excess triethyl-phosphite. The residue solubilized in 10 ml of ethanol undergoes chromatography on a silica column (5×56 cm) eluting first with 4 liters of a 95:5 ethyl-acetate/ethanol mixture and then with 3 liters of a 90:10 ethyl-acetate/ethanol mixture. 6.0 g (17.4 mmoles) of 1,4-benzene-diphosphonic acid tetra-ethyl ester are obtained with a molar yield of 41%.

Analysis: TLC, Silica F, (i) 90 ethyl-acetate/10 ethanol (ii) ethyl-acetate $^1$H-NMR ($CDCl_3$): δ1.35 (t, 12H, $CH_3$); 4.15 (m, 8H, $CH_2$); 7.92 (m, 4H, aromatic)

$^{31}$P-NMR: δ14.50

MS-EI: (M+) 350; m/e 321, 305, 294, 277, 238, 214, 158.

b) Preparation of 1,4-Benzene-Diphosphonic Acid 93 ml of HBr at 33% by weight in acetic acid are added to 6.68 g of 1,4-benzene-diphosphonic acid tetra-ethyl ester and the mixture is heated to 80° C. for 4 hours. After cooling to ambient temperature 200 ml of diethyl-ether are added and the mixture, after brief agitation, is cooled to −78° C. in a bath of ethanol and dry ice. The oily precipitate obtained is recovered by decantation and subjected twice more to the dispersion process with ether and low-temperature precipitation. The oily residue obtained is vacuum dried (1 mm Hg) at 50° C. for 8 hours, obtaining 4.0 g of 1,4-benzene-diphosphonic acid in the form of a white solid. Yield in moles 89%.

Analysis: TLC, Silica F, (i) 90 ethyl acetate/10 ethanol (ii) $75CH_3CN-25H_2O$ $^1$H-NMR (DMSO-$D_6$): δ7.8 (m, 4H, aromatic)

$^{31}$P-NMR: δ14.13 c) Preparation of Mesoporous Benzene-Diphosphonate/Phosphite of Zirconium 0.357 g of 1,4-benzene-diphosphonic acid and 0.574 g of phosphorous acid (C. Erba RPE Reagent), are dissolved in 38 ml of DMSO (dimethyl-sulphoxide) (C. Erba RPE), in a plastic container. To the clear solution, kept at 80° C., 0.806 g of $ZrOCl_2.8H_2O$ (Merk, RPE Proanalysis) are added dissolved in 1.55 ml of concentrated HF (50% by weight, C. Erba RPE) and 0.5 ml of water. The solution remains clear and has the following composition: $[C_6H_4(PO_3H_2)_2]=0.38M$, $[H_3PO_3]=0.175M$, $[Zr^{IV}]=0.063M$. The solution is kept at 80° C. for 24 hours, taking care that the volume remains constant. After this time the micro-crystalline solid that has formed is separated from the solution by centrifugation, washed twice with about 50 ml of DMSO and 3 times with about 50 ml of acetone, and lastly dried in an oven at 60° C. The solid zirconium diphosphonate/phosphite thus obtained is kept in a vacuum drier containing phosphoric anhydride.

Figure 4:
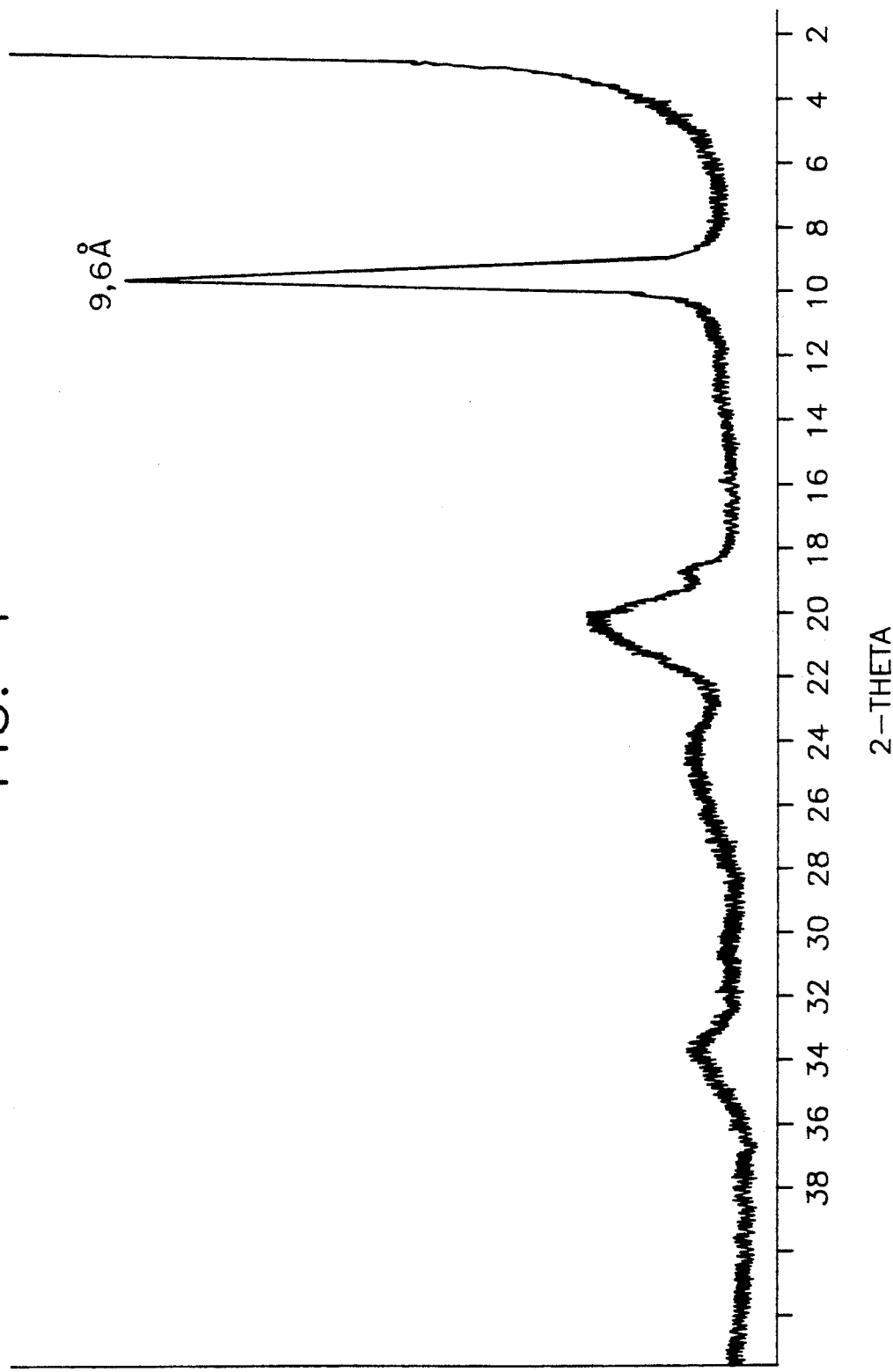

The X-ray diffraction spectrum of the powders is shown in FIG. 4 and illustrates typical reflections of an alpha-type structure, giving a distance between layers of 9.6 Å. To determine the diphosphonic acid/phosphorous acid molar ratio in the solid, the $^{31}$P nuclear magnetic resonance technique is used. About 20 mg of the solid are dissolved in a few drops of concentrated hydrofluoric acid, mixed with a few ml of DMSO and analysed with a Bruker 200 Spectrometer. The molar ratio is 0.7:1.

Figure 5:
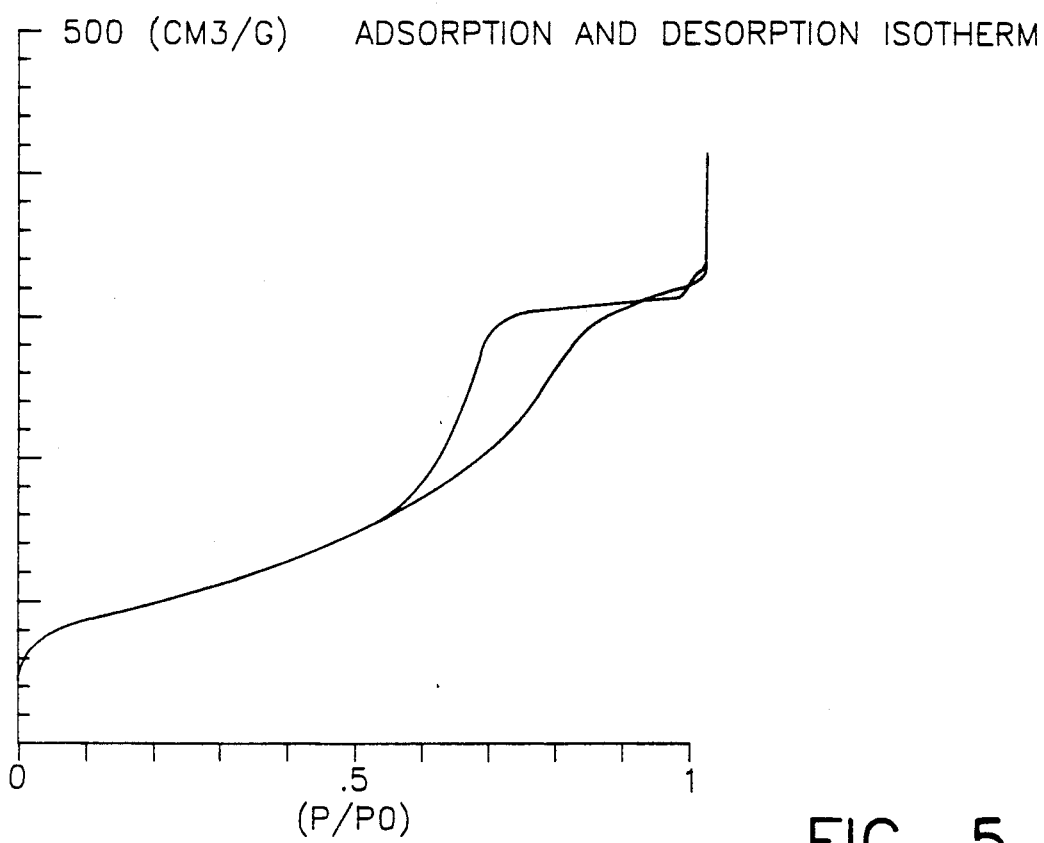
Figure 5:
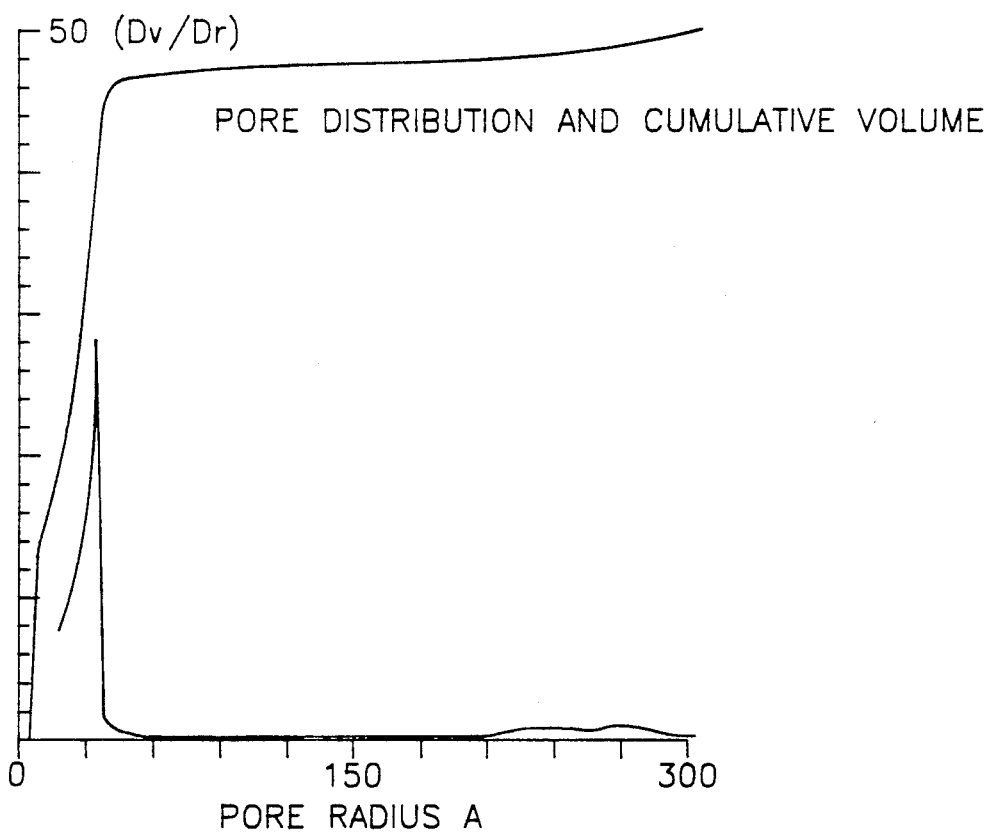

To find out the porosity characteristics the solid is first degassed at a temperature of 125° C. and at a pressure of $5\times10^{-3}$ torr. for 6 hours. A measurement is then made of the surface area by adsorption of nitrogen using a C. Erba Sorptomatic 1800 instrument. The adsorption and desorption isotherm illustrated in FIG. 5 shows an hysteresis loop which is typical of mesoporous solids. Mathematical treatment of the isotherm according to the BET theory gives a surface area of 360 $m^2/g$ and the pore distribution curve shows a single maximum peak corresponding to pores with a radius of 33 Å. From this curve it is calculated that 65% of the total porosity is between 35 and 20 Å.

EXAMPLE 2

Preparation of Mesoporous Dimethyl-Biphenyl Diphosphonate/Phosphite of Zirconium a) Preparation of 4,4'-bis (Hydroxy-Methyl) Biphenyl 789 mg (20.8 mmoles) of $LiAlH_4$ in 150 ml of anhydrous THF (tetrahydrofuran) are placed in a 2-liter flask which has a mechanical agitator, cooler, filler funnel and heating bath. A solution, heated to 50° C., of 7.5 g (27.7 mmoles) of 4,4'-bis (methoxycarbonyl)biphenyl in 500 ml of anhydrous THF is added dropwise, over a period of 1 hour, to the mixture, heated in an inert atmosphere to 50° C. under agitation. After a further 30 minutes of agitation in a heating bath, the mixture is cooled to ambient temperature and the excess LiAlH$_4$ is destroyed by the careful addition of 15 ml of a THF/H$_2$O (80:20) mixture. The reaction mixture is filtered on Septum G2, washing the precipitate with anydrous ethanol (3×100 ml). The combined filtrate and washings are evaporated to dryness under vacuum with the heating bath at 40° C. The residue is then redissolved with 100 ml of hot acetone (50° C.), eliminating the insoluble residue by filtration, dried on anhydrous Na$_2$SO$_4$ and evaporated to dryness. 5.74 g of 4,4'-bis (hydroxymethyl) biphenyl are obtained with a molar yield of 96.6%.

Analysis: Melting Point: 195.8°–196° C.

$^1$H-NMR (DMSOD$_6$): δ4.53 (d, 4H, CH$_2$); 5.20 (t, 2H, OH); 7.35–7.65 (8H, aromatic)

MS-EI: (M+)214; m/e 196, 183, 167, 165, 155, 152, 77.

b) Preparation of 4,4'-Bis (Bromomethyl) Biphenyl 11.6 g (54.13 mmoles) of 4,4'-bis (hydroxymethyl) biphenyl, 35.3 ml of HBr at 48% by weight in H$_2$O (649.6 mmoles) and 19.11 ml of H$_2$SO$_4$ at 96% are placed in a three-necked 500 ml flask which has a mechanical agitator, cooler and oil heating bath. The mixture is heated to 135° C. under vigorous agitation for 4 hours, after the first two hours adding to the very dense mixture an additional 7.4 ml of HBr at 48% and 2 ml of H$_2$SO$_4$ at 96%. On completion the cooled mixture is filtered on a Gooch G2 and the precipitate recovered is washed with iced water until the washings are neutral (about 1 liter). The solid residue is extracted with three 100 ml-portions of hot toluene (50° C.) and the extract is filtered hot. The toluene solution is concentrated dry at a reduced pressure and the residue dried at 40° C. using a high-vacuum pump. 16.97 g of 4,4'-bis (bromomethyl) biphenyl are obtained with a molar yield of 92.2%.

Analysis: Melting Point: 173.5° C.

$^1$H-NMR (DMSOD$_6$): δ4.75 (s, 4H, CH$_2$); 7.50–7.70 (8H, aromatic)

MS-EI: (M+) 338, 340, 342; m/e 261, 259; m/e 181; m/e 180; m/e 178; m/e 90 c) Preparation of 4,4'-bis(phosphonomethyl) biphenil acid tetra-ethyl ester 16.97 g (49.9 mmoles) of 4,4'-bis (bromomethyl) biphenyl and 52.04 ml (299.4 mmoles) of triethyl-phosphite are placed in a 250 ml flask which has a cooler and oil heating bath. The mixture is heated to 140° C. under magnetic agitation for 5 hours. On completion the excess triethyl-phosphite is separated by distillation and the white solid residue, redissolved in 50 ml of ethanol, is evaporated to dryness under vacuum, this operation being repeated twice. The residue is dissolved in 30 ml of ethanol and poured slowly into a beaker containing water and ice. The precipitate obtained is filtered on porous septum G3, washed with iced water (1 l) and under vacuum dried in an oven at 40° C., obtaining 21.02 g of 4,4'-bis (phosphonomethyl) biphenyl acid tetra-ethyl ester with a molar yield of 92.8%.

Analysis: Melting Point: 113.8° C.

TLC-Silica Gel (CH$_3$CN—H$_2$O 40:10)

$^1$H-NMR (DMSO-D$_6$): δ1.28 (t, 12H, CH$_3$); 3.20 (d, 4H, CH$_2$P); 4.05 (m, 8H, CH$_2$Et); 7.30–7.60 (8H, aromatic)

d) Preparation of 4,4'-bis (phosphonomethyl) biphenyl acid 21.02 g (46.3 mmoles) of 4,4'-bis (phosphonomethyl) biphenyl tetraethyl-ester and 100 ml of HBr at 33% by weight in acetic acid are placed in a 250 ml flask which has a cooler, magnetic agitation and heating bath. The mixture is heated under agitation at 80° C. for 5 hours, destroying the vapours with an additional cold-finger cooler filled with acetone and dry ice. The cooled mixture is poured under agitation into a beaker containing 200 ml of ice and distilled water and the precipitate that forms is filtered and washed with iced water (3×100 ml) and ethyl-ether (100 ml). The white solid obtained is dried using a mechanical pump obtaining 15 g of 4,4'-bis (phosphonomethyl) biphenyl acid, with a molar yield of 95.3%.

Analysis: Melting Point: >312° C.

$^1$H-NMR (DMSO-D$_6$): δ3.05 (d, 4H, CH$_2$); 7.20–7.70 (8H, aromatic)

$^{31}$P-NMR (DMSO-D$_6$): δ23.02 (external reference H$_3$PO$_4$).

e) Preparation of Mesoporous Dimethyl-Biphenyl Diphosphonate/Phosphite of Zirconium 0.684 g of bis (1,4-phosphonomethyl) biphenyl acid and 1.312 g of phosphorous acid are dissolved in 37 ml of DMSO in a plastic container kept at a temperature of 80° C. 1.611 g of ZrOCl$_2$.8H$_2$ dissolved in 2 ml of oncentrated HF and 1 ml of water are added. The solution is left in a water bath at 80° C. for 24 hours taking care that appreciable variations in volume do not occur. The solid that forms is separated from the solution, washed, dried and analysed as described in Example 1, Part c, gives a diphosphonic acid/phosphorous acid molar ratio of 0.8:1, by $^{31}$P NMR technique, and a distance between layers of 13.6 Å. The quantity of acid diphosphonate groups, determined by titrating 1 g of solid dispersed in 100 ml of NaCl 0.1M, with NaOH 0.1M up to pH=7, is equal to 0.3 mmoles/g. Measurement of the surface area gives a value of 330 m$^2$/g with a distribution of porosity concentrated at a maximum at 21 Å.

EXAMPLE 3

Preparation of Mesoporous Biphenyl-Diphosphonate/Phosphite of Zirconium a) Preparation of 4,4'-biphenyl-diphosphonic acid tetra-ethyl ester In an inert atmosphere (N$_2$), 22.2 ml (172 mmoles) of diethylphosphite and 65 ml of hexamethyl-phosphoramide are placed in a three-necked 500 ml flask which has a mechanical agitator and cooler. 4.1 g (172 mmoles) of NaH are added to the solution very carefully and under slow agitation. When hydrogen is no longer generated, 32.7 g (172 mmoles) of CuI and 13.3 g (43 mmoles) of 4,4'-dibromo-biphenyl are added to the mixture heated to 70° C. under agitation. The reaction mixture is heated to 170° C. and kept under agitation for 2.5 hours. After cooling, the mixture is transferred to a 5-liter flat-bottomed conical flask and after adding 2 liters of ethyl-ether and 1.5 liters of H$_2$O, left under vigorous agitation for 1 hour. After filtering the solid phase on a Gooch, the double liquid phase is separated with a separator funnel recovering the ether layer. Both the aqueous and the solid phase are further washed with diethyl-ether (total 1 liter) and the combined organic extracts are evaporated to dryness under vacuum. The residue is redissolved twice with absolute ethanol and evaporated to dryness under vacuum, obtaining 25 g of raw material. The material is purified by chromatography on a silica column (5×56 cm) eluting first with a mixture of ethyl-acetate/ethanol (95:5) to eliminate the by-products and then with ethyl-acetate/ethanol (50:50), recovering 4.9 g of 4,4'-biphenyl diphosphonic acid tetra-ethyl ester with a molar yield of 26.7%.

Analysis: TLC, Silica F, (i) 25. ethyl-acetate/75 oil ether (ii) 90 ethyl-acetate/10 ethanol MS-EI: (M+) 426; m/e 398, 381, 370, 353, 317, 314, 152

$^1$H-NMR (CDCl$_3$): δ1.35 (t, 12H, CH$_3$); 4.15 (m, 8H, CH$_2$); 7.7–8.0 (8H, aromatic)

$^{31}$P-NMR: δ16.1 b) Preparation of 4,4'-Biphenyl-Diphosphonic Acid 66 ml of HBr at 33% by weight in acetic acid are added to 4.9 g (11.5 moles) of 4,4'-biphenyl-diphosphonic acid tetra-ethyl ester and the mixture is heated at 80° C. for 4 hours. After cooling to ambient temperature, 150 ml of H$_2$O are added under agitation and the precipitate obtained is filtered, washed with water and vacuum dried (20 mm Hg) at 45° C. for one night. 2.29 g of 4,4'-biphenyl-diphosphonic acid, with a molar yield of 66% are obtained.

Analysis: TLC, Silica F, (i) 75CH$_3$CN—25H$_2$O (ii) 90 ethyl-acetate/10 ethanol $^1$H-NMR (CDCl$_3$): δ7.80 (8H, aromatic)

$^{31}$P-NMR: δ14.82 c) Preparation of Mesoporous Biphenyl-Diphosphonate/Phosphite of Zirconium 0.19 g of 4,4'-(biphenyl) diphosphonic acid and 0.77 g of phosphorous acid are dissolved in 18 ml of DMSO in a plastic container kept at a temperature of 80° C. 0.80 g of ZrOCl$_2$.8H$_2$O dissolved in 1.5 ml of concentrated HF and 1 ml of water, are added to the clear solution. The solid obtained after 24 hours, separated, washed, dried and analysed as described in Example 1, gave a diphosphonic acid/phosphorous acid molar ratio of 0.8:1 and a distance between layers of 14 Å. Measurement of the surface area gives a value of 300 m$^2$/g with a pore distribution concentrated at a maximum at 22 Å.

EXAMPLE 4

Preparation of Zirconium Benzene-Diphosphonate 1.2 g of 1,4-benzene-diphosphonic acid are dissolved in 38 ml of DMSO and kept in a water bath at a temperature of 80° C. 1.611 g of ZrOCl$_2$.8H$_2$O dissolved in 1.5 ml of concentrated HF and 0.5 ml of water are added to the clear solution. The solid obtained after 24 hours, separated, washed, dried and analysed as described in Example 1, Part c, showed a distance between layers of 9.6 Å. Measurement of the surface area gives a value of 110 m$^2$/g and the pore distribution curve has no relative maximum peaks.

EXAMPLE 5

Preparation of Benzene-Diphosphonate/Phosphite of Zirconium 0.571 g of 1,4-benzene-diphosphonic acid, prepared as described in Example 1, and 1.114 g of phosphorous acid are added to a solution of 7 ml of DMSO and 20 ml of water kept at a temperature of 80° C. in a plastic container. A solution comprising 0.773 g of ZrOCl$_2$.8H$_2$O dissolved in 1.2 ml of concentrated HF and 1.8 ml of water are added to the clear solution. The solid obtained after 24 hours at 80° C., is treated as described in Example 1, Part c, and has a diphosphonic acid/phosphorous acid molar ratio of 1.9:1. The distance between layers, determined from the X-ray diffraction spectrum of the powders is 9.6 Å. The nitrogen adsorption and desorption isotherm shows no hysteresis loops, the surface area is 250 m$^2$/g and the pore distribution has no relative maximum peaks.

EXAMPLE 6

Preparation of Dimethyl-Biphenyl-Diphosphonate/Phosphite of Zirconium 1.368 g of 4,4'-bis (phosphonomethyl) biphenyl acid, prepared as described in Example 3, and 0.984 g of phosphorous acid are dissolved in 37 ml of DMSO kept in a plastic container at 80° C. A solution comprising 1.66 g of ZrOCl$_2$.8H$_2$O dissolved in 2 ml of concentrated HF and 1 ml of water is added to the clear solution. The solid obtained after 24 hours at 80° C., separated from the solution, washed, dried and analysed as described in Example 1, Part c, has a diphosphonic acid/phosphorous acid molar ratio of 1.5:1. The distance between layers is 13.8 Å. The nitrogen adsorption and desorption isotherm conducted and interpreted according to the BET theory gives a surface area of 250 m$^2$/g and a statistical pore distribution curve.

EXAMPLE 7

Preparation of Dimethyl-Biphenyl-Diphosphonate/Phosphite of Zirconium 0.684 g of 4,4'-bis (phosphonomethyl)biphenyl acid prepared as described in Example 3 and 2.952 g of phosphorous acid are dissolved in 36 ml of dimethyl-sulphoxide kept in a plastic container at 80° C. A solution comprising 3.22 g of ZrOCl$_2$.H$_2$O dissolved in 3.4 ml of concentrated hydrofluoric acid and 1 ml of water is added to the clear solution. The solid obtained after 24 hours at 80° C., separated from the solution, washed, dried and analysed in accordance with the procedures described in Example 1, has a diphosphonic acid/phosphorous acid molar ratio of 0.3:1. The distance between the layers of the compound, equal to 19.5 Å, can be interpreted by the formation of asymmetrical layers as described in the publication by G. Alberti, U. Costantino and G. Perego, quoted above. The nitrogen adsorption and desorption isotherm conducted and interpreted according to the BET theory gives a surface area value of 140 m$^2$/g and a pore distribution curve with a weak maximum around 23 Å. The fraction of porosity within 20 and 25 Å is about 5%.

We claim:

1. A compound comprising a diphosphonate of a tetravalent metal containing acid phosphite groups and diphosphonate groups fixed to the surface, which can be defined by the general formula

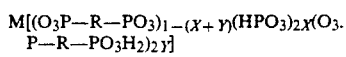

Where:
M is zirconium;
R is selected from among the aliphatic bivalent organic radicals containing in the molecule from 2 to 10 carbon atoms, or the aromatic radicals with 1 to 2 uncondensed rings, or the alkyl-aromatic radicals;

X varies from 0.3 to 0.45; and the compound being in the form of a crystalline solid having the following characteristics an Alpha type lamellar structure with a distance between layers of 7.4 to 20 Å;

a BET surface area of 250 to 400 $M^2/g$; and porosity within the mesopore range, with at least 50% of the pores measuring 20 to 30 Å.

2. A compound according to claim 1, characterised in that the R radical is selected from $-CH_2-CH_2-$, $-CH_2-(CH_2)_2-CH_2-$, $-CH_2-(CH_2)_4-CH_2-$, $-C_6H_4-$, $-C_6H_4-C_6H_4-$ and $-CH_2-C_6H_4-C_6H_4-CH_2-$.

3. A compound according to claim 1, characterised in that microporosity may or may not be present in the region between layers.

4. A process for the preparation of the compound according to claim 1, characterised in that a diphosphonic acid $R(PO_3H_2)_2$, phosphorous acid $H_3PO_3$ and the oxychloride of a tetravalent metal $MOCl_2$ are made to react:

$(1-x+y)R(PO_3H_2)_2 + 2xH_3PO_3 + MOCl_2 \longrightarrow$

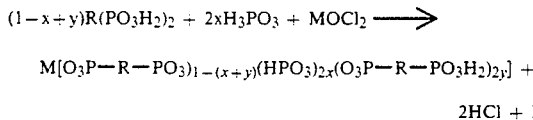

$+ 2HCl + H_2O$ (where M, R, x, y have the meaning given above) in a solvent comprising sulphoxide/water containing hydrofluoric acid.

5. A process according to claim 4, characterised in that the diphosphonic acid is selected from 1,4-benzene diphosphonic acid, 4,4'-bis (phosphonomethyl) biphenyl acid and 4,4'-bis (biphenyl) diphosphonic acid.

6. A process according to claim 4, characterised in that the oxychloride of a tetravalent metal is selected from an octahydrate $ZrOCl_2.8H_2O$ zirconyl chloride and monohydrate $ZrOCl_2.H_2O$ zirconyl chloride.

7. A process according to claim 4, characterised in that the molar ratio between diphosphonic acid plus phosphorous acid and the oxyhalide of a tetravalent metal is from 2:1 to 20:1.

8. A process according to claim 4, characterised in that a concentrated aqueous solution of hydrofluoric acid is used, the molar ratio of said acid to the tetravalent metal being of from 6:1 to 30:1.

9. A process according to claim 4, characterised in that the reaction medium is a mixture of dimethyl-sulphoxide and water.

10. A process according to claim 4, characterised in that the reaction temperature varies from 10° to 130° C. and the reaction time varies from 10 to 100 hours.

11. A process according to claim 10, characterised in that the said temperature is of the order of 80° C. and the period is about 24 hours.

12. A process according to claim 4, characterised in that the diphosphonate/phosphite of tetravalent metal is recovered from the reaction mixture by filtration or centrifugation, is then washed with an organic solvent and lastly dried.

13. The use of the compound according to claim 1 as a molecular sieve or as a basis for the production of shape selective catalysts.

* * * * *

UNITED STATES PATENT AND TRADEMARK OFFICE
CERTIFICATE OF CORRECTION

PATENT NO. : 5,166,380
DATED : November 24, 1992
INVENTOR(S) : Giulio Alberti et al.

It is certified that error appears in the above-identified patent and that said Letters Patent is hereby corrected as shown below:

Column 11:

In Claim 1, after "X varies from 0.3 to 0.45; and", there should be inserted —Y varies from 0.05 to 0.2;—.

Signed and Sealed this

Ninth Day of November, 1993

Attest:

BRUCE LEHMAN

*Attesting Officer*   *Commissioner of Patents and Trademarks*